United States Patent [19]
Weiss

[11] Patent Number: 5,184,274
[45] Date of Patent: Feb. 2, 1993

[54] ADJUSTABLE, ELASTIC STATIC CONTROL WRISTBAND

[75] Inventor: John W. Weiss, St. Paul, Minn.

[73] Assignee: Minnesota Mining and Manufacturing Company, St. Paul, Minn.

[21] Appl. No.: 579,168

[22] Filed: Sep. 7, 1990

[51] Int. Cl.⁵ ............................................. H05F 3/00
[52] U.S. Cl. .................................. 361/220; 361/212
[58] Field of Search .............. 361/212, 220, 223, 224; 63/3, 4; 439/37; 2/170; 224/164, 175, 178; 368/286, 293

[56] References Cited

U.S. PATENT DOCUMENTS

| | | | |
|---|---|---|---|
| 3,015,754 | 1/1962 | Legge | 361/223 |
| 3,830,414 | 8/1974 | Caprielian | 63/3 X |
| 4,577,256 | 3/1986 | Breidegam | 361/220 |
| 4,885,728 | 12/1989 | Gosselin | 361/212 X |
| 5,036,423 | 7/1991 | Williams | 361/212 |

OTHER PUBLICATIONS

EOS/ESD Standard No. 1, published by EOS/ESD Association, Inc., Jan. 1987.

Primary Examiner—A. D. Peilinen
Assistant Examiner—Fritz M. Fleming
Attorney, Agent, or Firm—Gary L. Griswold; Walter N. Kirn; Jack V. Musgrove

[57] ABSTRACT

An adjustable, elastic wristband for dissipating the buildup of excess electrostatic discharge from an individual. The wristband has two straps or strap sections, one electrically insulative and the other electrically conductive, and at least one of the two straps or strap sections being elastic. A connector case provides the electrical connection between the conductive strap and a conductive grounding tether. Various clasps are used to adjust the insulative strap or strap section. In each of the disclosed alternative embodiments, the wristband may be adjusted for comfort without requiring trimming of the excess strap material which is pulled through the clasp, and without otherwise exposing any conductive portions of the wristband, since the excess adjusted material is electrically insulative and thus may be left dangling.

18 Claims, 5 Drawing Sheets

ADJUSTABLE, ELASTIC STATIC CONTROL WRISTBAND

BACKGROUND OF THE INVENTION

1. Field of the Invention

The present invention generally relates to devices for preventing electrostatic discharge, and more particularly to an adjustable, elastic static control wristband.

2. Description of the Prior Art

Electrostatic discharge, as well as the mere presence of a static electric field, can be extremely detrimental to sensitive electronic parts. This is particularly true of modern semiconductors and integrated circuits which may be degraded or destroyed by the buildup of static electricity in the workplace. Especially sensitive components can be severely affected by an electrical potential as small as 50 volts, yet the simple act of walking has been known to triboelectrically generate a potential of 30,000 volts or more.

The most common tool heretofore used in the battle against electrostatic discharge is a conductive tether which is designed to drain away excess electrostatic charge. One of the earliest grounding tethers is described in U.S. Pat. No. 3,015,754 issued to W. Legge, which illustrates a grounding strap for a human leg, with a tether connecting the strap to a conductive tread to be attached to the bottom of a shoe. Later devices incorporated a wristband, and there are several variations of the wristband and/or grounding tether.

The subject invention relates to an elastic static control wristband which has improved adjustability. Several patents disclose adjustment mechanisms in wrist or body straps. For example, the simplest adjustment device is a conventional buckle, such as that shown in U.S. Pat. No. 4,677,521. The primary disadvantage of such a device is that it must be manipulated each time the wristband is put on or taken off. This is also true for over-center snap type buckles such as that shown in French Patent 2,607,014 (see figure 3 of that patent). Moreover, the extent to which such buckles are adjustable is extremely limited. In other words, several different sizes must be provided for users with different sized wrists. It is also difficult to achieve a proper exact adjustment with these devices, since they provide only discrete adjustment settings. This is critical to the performance of the wristbands, since they must have good contact with the skin, and yet not be so tight to constrict circulation or otherwise be uncomfortable.

Figure 1:
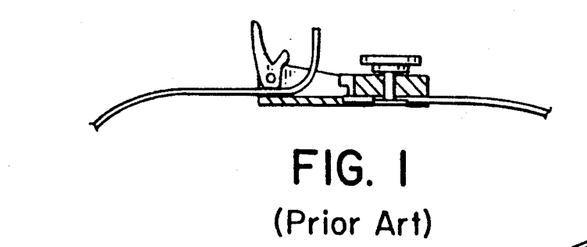
FIG. 1 is a cross-sectional view of a prior art clasp for a static control wristband.

There are many alternatives to the standard buckle, such as the prior art clasp depicted in FIG. 1, which is also shown in U.S. Pat. No. 4,577,256 (see FIGS. 3 and 4 of that patent). This clasp utilizes a gate having a jam which firmly grasps the end of an elastic, conductive strap. The primary problem with this construction is that the loose (conductive) end of the strap which dangles from the clasp may come into contact with an electrical power source, presenting a hazard to the user. This construction is thus somewhat inconsistent with the statement in that patent (at column 4, lines 53–59) that the clasp body should be made of an antistatic material in order to avoid such an inadvertent contact with a power source. Of course, the free end of the strap may be cut off, but this creates the highly undesirable potential for unraveling of the material or release of small fibers into the work area which can damage the electronic components being handled. After cutting, it would also be impossible to readjust the wristband to fit a larger wrist. Similar clasp constructions are described in U.S. Pat. Nos. 4,639,825; 4,662,695; 4,680,668; 4,720,765; 4,755,144; and 4,782,425.

Figure 2:
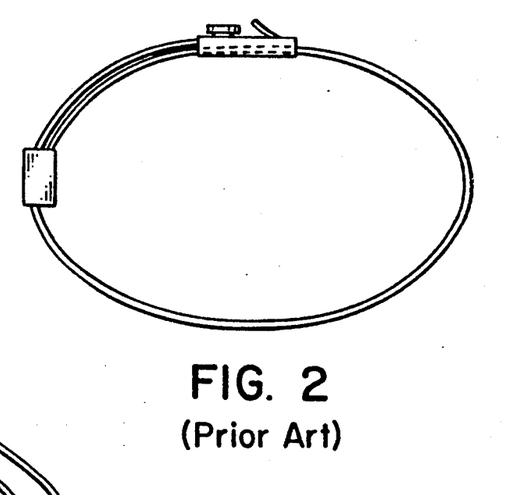
FIG. 2 is a side elevational view of a prior art adjustable, elastic static control wristband, wherein the strap is constructed of a conductive material and the adjustable end is loosely attached to the strap.

One variation on an adjustable wristband which overcomes several of the above-noted problems is shown in FIG. 2, this variation also being depicted in U.S. Pat. No. 4,577,256 (see FIG. 8 of that patent, and figures 10–11 which show a similar design). In this design, one end of the elastic, conductive strap passes through the clasp and is held loosely against the other portion of the strap by a guide. A gate/jam is still used to fix the effective length of the strap. One significant disadvantage in the design of FIG. 2 is that it is incompatible for use with dual-conductor type wristbands (such as that shown in FIG. 13 of U.S. Pat. No. 4,639,825). Furthermore, when this wristband is stretched and then relaxed over the wrist, the inner, overlapping portion may creep out from under the overlying strap, and may similarly create comfort problems when the overlapping portion of the strap curls onto itself.

Figure 3:
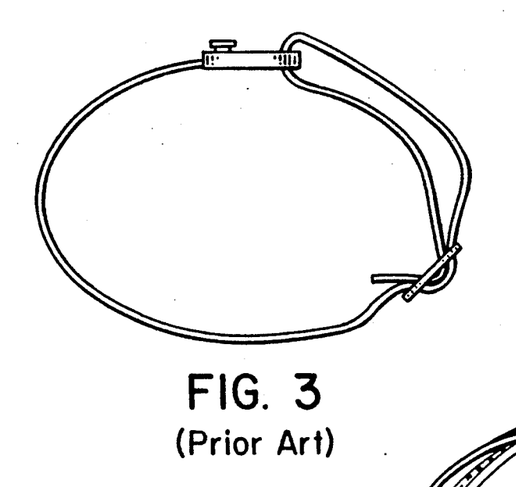
FIG. 3 is a side elevational view of another prior art adjustable, elastic static control wristband wherein the strap has an outer insulative surface and an inner conductive surface, one end of the strap being folded inwardly.

Another prior art construction is shown in FIG. 3 which utilizes a strap material that has an insulative outer surface and a conductive inner surface. The strap material is folded back and held in place by a figure-8 ring. Such a wristband is produced by Light Year Industrial Co., and is similar to the construction shown in U.S. Pat. No. 4,816,964 (see FIG. 9 of that patent). A simpler version (with a plain conductive fabric strap) is also shown in U.S. Pat. No. 3,015,754. This construction is advantageous because it confines the free end of the strap within the loop formed by the rest of the strap. In other words, the free end is held between the strap and the skin of the user, and cannot inadvertently contact a power source. The problem with this construction, however, is that the loop back or folded portion of the strap reduces the effective length of the inner conductive surface. In other words, it is the outer insulative surface which contacts the skin along the folded area of the strap. On small wrists, this folded material can effectively cover all of the conductive inner surface rendering the fabric element of the wristband useless. Although this problem may be avoided by folding the strap outwardly in an opposite manner, this would then expose the inner conductive surface and re-create the aforementioned safety hazard. Another problem with this construction is that the folded portion will only stretch half as much as the unfolded portion for any given pulling force, meaning that the unfolded portion will undergo greater stresses in use and wear out sooner.

Figure 4:
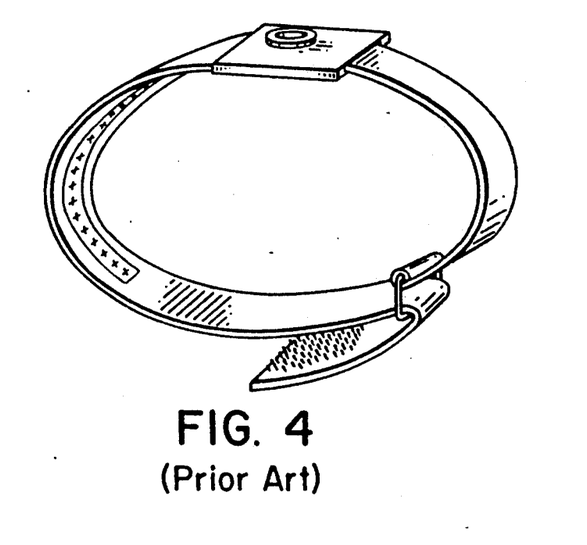
FIG. 4 is a perspective view of a prior art adjustable, inelastic static control wristband.

Another exemplary prior art adjustable wristband is shown in FIG. 4, which utilizes a D-ring to buckle two inelastic strap portions together. The straps are formed from a fabric which has a conductive portion along the center of the inner surface of the fabric. The free end is secured to the D-ring by a hook-and-loop fastener. Although this construction does not expose any conductive material, it suffers from the same drawbacks as the conventional buckle, i.e., it must be manipulated when put on and taken off, and the user may easily fit it loose for comfort, but resulting in poor skin contact.

Other variations of prior art adjustable wrist straps suffer one or more of the above disadvantages. For example, U.S. Pat. No. 4,847,729 discloses a SPEIDEL ™ -type wristband (a chain of expandable metallic links) for use with static control. The only method of adjusting this kind of wristband, however, is to add a plurality of modified (inelastic) links, which is tedious, reduces the active expansion link percentage, and still only provides discrete expansion settings.

It would, therefore, be desirable and advantageous to design a static control wristband which allows the user to optimize the sizing of the wristband for a comfortable fit, without creating safety concerns or requiring the need of removal of excess conductive strap material. The design should also accommodate dual conductor wristband variations.

SUMMARY OF THE INVENTION

The foregoing objective is achieved in a static control wristband having two straps or strap sections, one electrically insulative and the other electrically conductive, and at least one of the two straps or strap sections being elastic. A connector case is also necessary to provide the electrical connection between the conductive strap and a grounding tether, and clasp means are used to adjust the insulative strap.

In one embodiment, a single integral, elastic strap is divided into two sections, one having a conductive portion along its inner surface, and the other being completely insulative. The conductive section is in contact with a metallic snap placed on the connector case, while the insulative section passes through a clasp, such as a figure-8 ring. A first variation of this embodiment allows for an insulative strap separate from the elastic strap (conductive along its inner surface), but sewn or sonically welded to the conductive strap. Another variation splits the strap into left and right segments to accommodate a dual conductor type wristband. A further variation substitutes a SPEIDEL TM-type wristband for the elastic fabric strap.

In another embodiment of the invention, an inelastic strap, conductive at least on its inner surface, is surrounded by an elastic, insulative strap, the latter passing through the clasp, and the two straps being aligned by guides. The insulative strap is wider than the conductive strap in order to prevent exposure of the conductive strap to a power source. This allows the use of a cheaper fabric, e.g., one that is inelastic and is conductive on both its inner and outer surfaces. This embodiment may also me modified by affixing a metallized film to the inner surface of a nonconductive, inelastic fabric, or by substituting a non-expanding by flexible chain of metallic (conductive) links for the conductive fabric, or may further be altered for use as a dual conductor wristband. All of these embodiments provide greater adjustability and comfort without requiring trimming of the excess strap material which is pulled through the clasp, and without otherwise exposing any conductive portions of the wristband, since the excess adjusted material is electrically insulative and thus may be left dangling.

BRIEF DESCRIPTION OF THE DRAWINGS

The novel features and scope of the invention are set forth in the appended claims. The invention itself, however, will best be understood by reference to the accompanying drawings, wherein:

DESCRIPTION OF THE PREFERRED EMBODIMENTS

Figure 5:
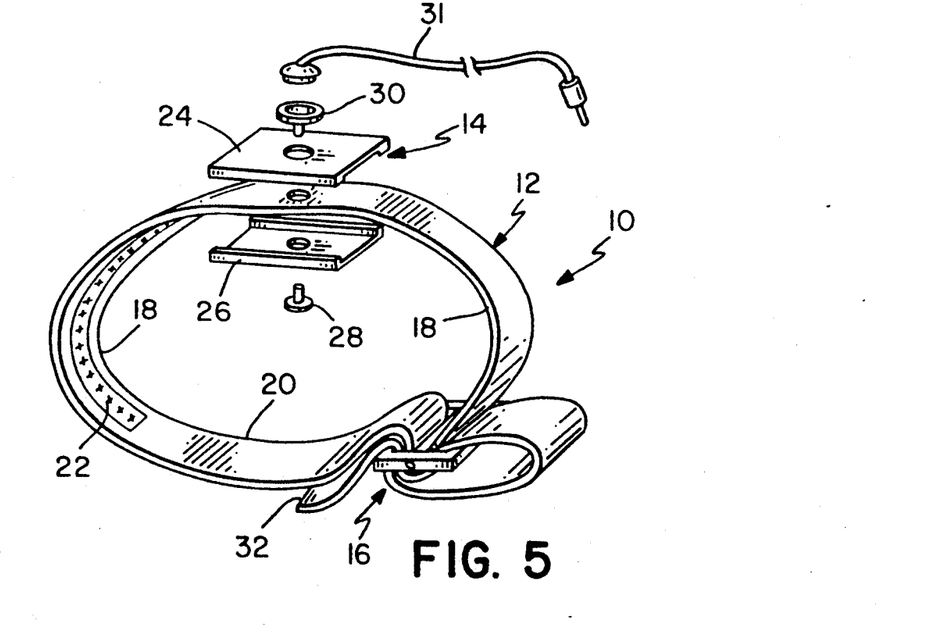
FIG. 5 is a perspective view of one embodiment of the adjustable, elastic static control wristband of the present invention, utilizing a fabric strap having two separate sections.

With reference now to the figures, and in particular with reference to FIG. 5, there is depicted the simplest embodiment 10 of the adjustable, elastic static control wristband of the present invention. Wristband 10 is generally comprised of a strap 12, a connector case 14 and a clasp 16. In this embodiment, strap 12 is a single piece of elastic fabric which is divided into two sections, 18 and 20. Section 18 has an electrically insulative outer surface, and a conductive portion 22 lying along its inner surface. Section 20 is completely insulative. A stretchweave fabric having this construction is available from Offray, Inc. of Chester, N.J. In that particular fabric, when the conductive yarns are not woven into the strap, they lie on the surface thereof and must be cut off. This cutting step may be performed during the manufacture of wristband 10. Strap 12 is typically about 2 centimeters wide, and should be long enough to accommodate a large wrist size, i.e., a total length of about 24 cm. Strap 12 preferably has an elongation of at least 1.5 which allows the wristband to pass around the hand of the user but still retract to fit snugly against the wrist, and also has a low spring rate for comfort, e.g., about 0.12 lbs/in.

Connector case 14, which typically includes a cover 24 and a backplate 26, engages a central portion of strap 12. A conductive (metallic) rivet 28 passes through holes in strap 12 and connector case 14, and secures a female snap connector 30. Connector 30 thereby makes electrical contact with conductive portion 22 of strap 12. Backplate 26 may also be metallic to enhance conductivity between the skin and connector 30, but cover 24 is preferably formed from an insulative material, e.g., polypropylene or polyethylene. Connector 30 is designed to receive one end of a conductive grounding tether 31, the other end of which may be electrically connected to the ground, i.e., zero electrical potential.

The free end of section 18 of strap 12 is affixed to clasp 16 which may take the form of a figure-8 ring; this end may be affixed to clasp 16 by looping it around the center bar of the figure-8 ring and sewing the end (or sonically welding it) onto itself. The free end 32 of section 20 is then threaded through clasp 16 to form a tight fitting cinch. The length effective of this section 20 may easily be adjusted by feeding more or less material through clasp 16. In this regard, the term "effective length, " of any strap or strap section, refers to that portion of the strap or strap section which would be in intimate contact with the user's wrist. Regardless of the amount of adjustment, free end 32 never presents a safety hazard inasmuch as it is completely insulative. Both ends of strap 12 are preferably fused to prevent unraveling or release of small fibers.

Figure 9:
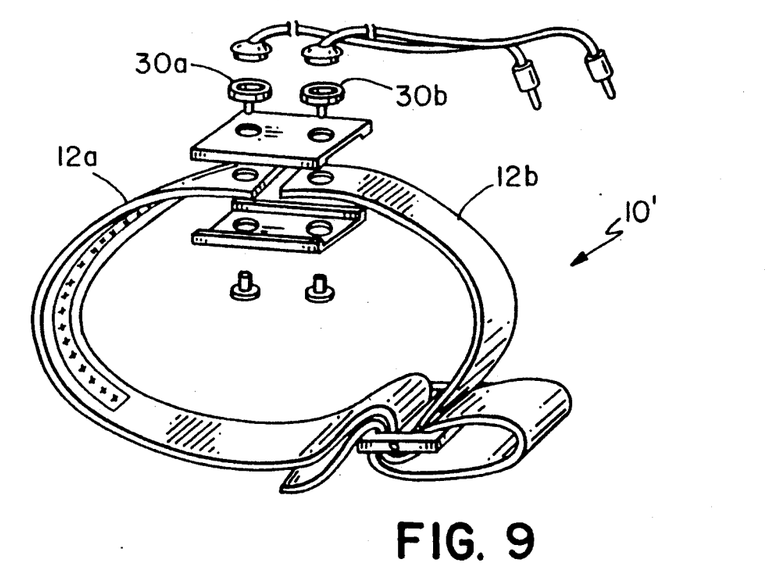
FIG. 9 is perspective view of one embodiment of the present invention utilizing an elastic fabric having two separate sections.

Clasp 16 may take other forms besides a figure-8 ring, such as (i) a clasp having spikes and a hinged cover to capture the fabric, (ii) a wedging gate or jam-type device as shown in FIG. 1, or (iii) a D-ring as shown in FIG. 4. The clasp should, however, be small and not materially reduce the amount of active expansion of strap 12 and, naturally, be electrically insulative. It will also be understood that, instead of providing a single strap having two integral sections 18 and 20, two separate straps may be provided, one having the conductive inner surface and the other being insulative. The two straps would then be sewn together or sonically welded. Those skilled in the art will further appreciate that the wristband of FIG. 5 may easily be modified to a dual conductor wristband by splitting the conductive section 18 of strap 12 into two separate segments, each attached to separate connectors. Such a wristband 10' is depicted in FIG. 9, having two straps 12a and 12b, each including conductive sections along the inner surfaces thereof. Straps 12a and 12b are electrically connected to connectors 30a and 30b, respectively.

Figure 6:
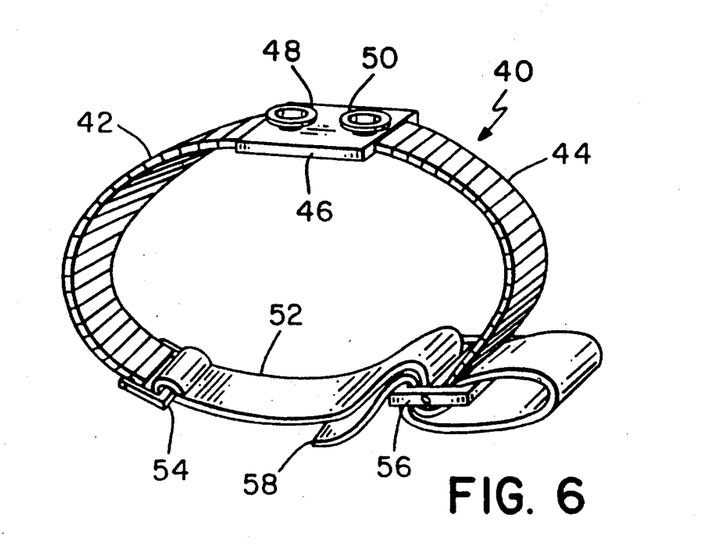
FIG. 6 is a perspective view of another embodiment of the present invention, utilizing an expandable chain of metallic links, having an insulative outer covering, and forming a dual conductor wristband.

Referring now to FIG. 6, a dual conductor wristband 40 embodiment of the present invention is shown which employs a plurality of metallic links forming two electrically isolated expandable chain segments 42 and 44. Appropriate chain material is available from Speidel (a division of Textron, Inc., of Providence, R.I.) under the brand name "Twist-0-Flex". The chain is conductive, at least along its inner surface, and preferably is insulative along its outer surface, e.g., by providing an insulative coating or affixing durable insulative caps. A connector case 46, similar to connector case 14 of FIG. 5, receives both segments 42 and 44. Connector case 46, however, houses two connectors 48 and 50 which ar in separate electrical contact with segments 42 and 44, respectively. A dual conductor grounding tether provides separate electrical pathways for each connector 48 and 50.

Figure 10:
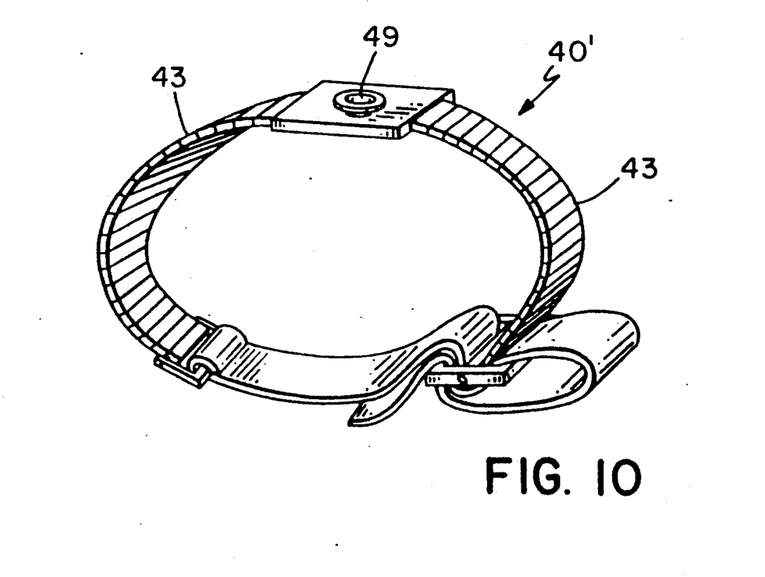
FIG. 10 is a perspective view of another embodiment of the present invention having two separate, non-expandable chain segments of metallic links.

The free end of chain segment 42 is attached to an electrically insulative strap 52 by means of a clip 54. Strap 52 is essentially identical to section 20 of strap 12, and is thus preferably, but not necessarily, elastic. In the preferred embodiment, chain segment 42 is attached to clip 54 by means of a spring-loaded pin, while strap 52 is attached thereto by looping it around a cross-bar of clip 54 and sewing the end (or sonically welding it) onto itself. Similarly, the free end of chain segment 44 is attached to another (figure-8 type) clasp 56 by a spring-loaded pin, and the free end 58 of strap 52 is then threaded through clasp 56 to form a tight fitting cinch. As with wristband 10, chain segments 42 and 44, together with strap 52, preferably have an elongation of at least 1.5, and a low spring rate. It is understood that the term "elastic" as used herein includes in its meaning the expandable nature of chain segments 42 and 44 since those segments provide a retracting force. Of course, a single conductor version of wristband 40 may be constructed by simply providing electrical continuity between chain segments 42 and 44. Alternatively, a single chain segment 43 may be used with the wristband 40' shown in FIG. 10. In this embodiment, segment 43 is in contact with a single connector 49.

Figure 7:
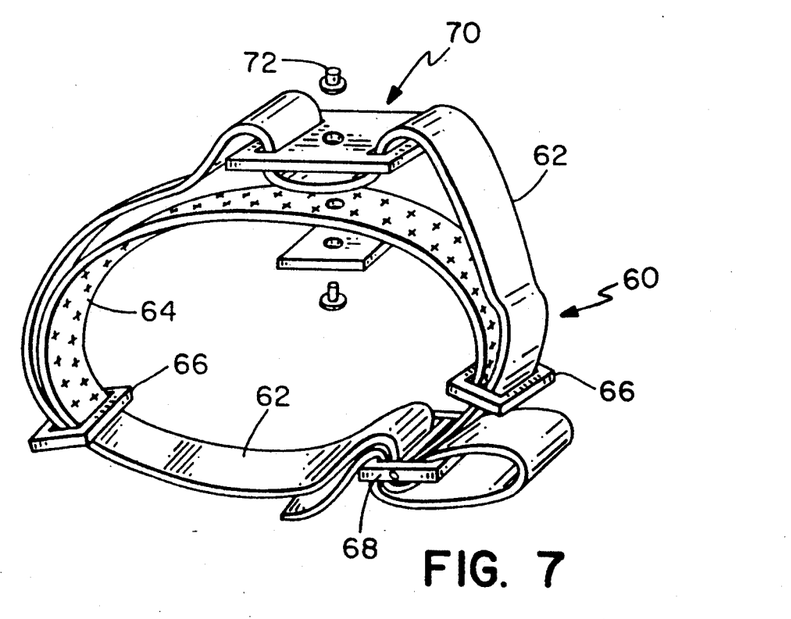
FIG. 7 is a perspective view of yet another embodiment of the present invention wherein an insulative, elastic strap surrounds a conductive, inelastic fabric strap.

Another wristband embodiment 60 of the present invention, illustrated in FIG. 7, utilizes an elastic, electrically insulative strap 62 and an inelastic, electrically conductive strap 64. Inelastic strap 64 may be formed from a fabric having conductive yarns; alternatively, strap 64 could be constructed by affixing a metallized film (or applying a conductive coating) to the inner surface of a strip of any insulative, durable material. In either case, strap 64 is preferably flexible along its longitudinal direction (length), to conform to contours of the wrist; however, it is preferably rigid along its transverse direction (width), and furthermore should not be easily compressed or rolled along its longitudinal direction. Strap 64 is also preferably relatively hard to inhibit penetration of any pointed object therethrough which might come into contact with the conductive inner surface.

Figure 11:
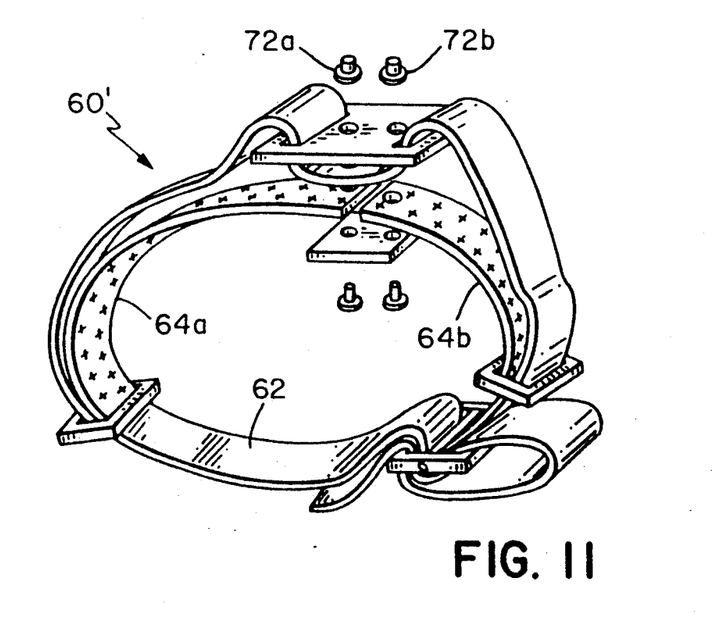
FIG. 11 is a perspective view of yet another embodiment of the present invention wherein an insulative, elastic strap surrounds two separate, conductive, inelastic strap section.

Strap 64 is loosely held against strap 62 by means of two guides (D-rings) 66. The ends of strap 64 are permanently attached to guides 66, but strap 62 is merely threaded through the guides. Strap 62 may be constructed of any elastic, electrically insulative material, including a simple stretchweave fabric. Strap 62 is preferably wider than strap 64 to insure that no conductive portion of strap 64 is exposed. The ends of strap 6z are held in adjustable relationship by another clasp 68. A connector case 70 is again provided, although FIG. 7 illustrates the use of a male snap connector 72 rather than a female snap connector. As with the previous embodiments, the design of FIG. 7 may be altered to provide a dual conductor wristband 60' as illustrated in FIG. 11. In this design, strap 64 has been cut into two inelastic, conductive straps 64a and 64b, which are attached to male studs 72a and 72b, respectively. It is not necessary, however, to so cut strap 62 since it is insulative.

Figure 8:
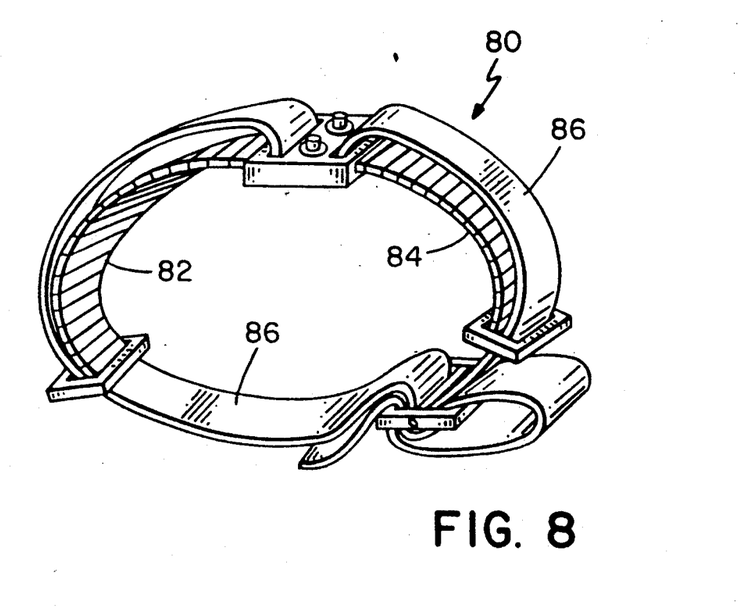
FIG. 8 is a perspective view of still another embodiment of the present invention similar to that shown in FIG. 7 except that a nonexpandable chain of conductive links has been substituted for the inelastic fabric strap.
Figure 12:
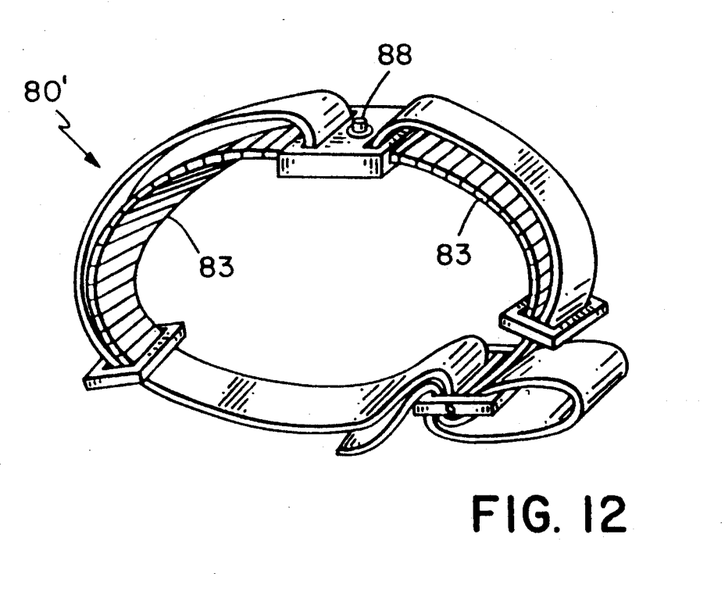
FIG. 12 is a perspective view of still another embodiment of the present invention wherein an insulative, elastic strap surrounds a non-expandable chain of conductive links.

With further reference to FIG. 8, another wristband embodiment 80 of the present invention is depicted which is very similar to the wristband 60 of FIG. 7. In fact, wristband so is essentially identical to wristband 60 except that flexible chain segments 82 and 84 have been substituted for strap 64. Also, FIG. 8 depicts a dual conductor version of the two-strap wristband, i.e., the two chain segments 82 and 84 are separately connected to two male snap connectors. An elastic, insulative strap 86, identical to strap 62, is aligned with chain segments 82 and 84 with guides, as before, and another clasp provides adjustability to strap 86. Although chain segments 82 and 84 may be expandable, they preferably are not, since expanding links, when retracting, may pinch the skin or grab body hair, creating discomfort. The chain segments are, nevertheless, flexible to conform to the shape of the wrist. Nonexpandable chain segments with an outer strap may likewise be used to create a single conductor wristband; as with the single conductor wristband 40' of FIG. 10, such a wristband could be constructed by simply providing electrical continuity between chain segments 82 and 84. Alternatively, a single nonexpandable chain 83 may be used with the wristband 80' depicted in FIG. 12. In this construction, chain 83 is connected to a single male snap connector 88.

Each of the foregoing embodiments presents a wristband which allows a wide degree of adjustment for comfort and yet, due to the elasticity of at least one of the straps, insures proper electrical contact with the skin of the user. Furthermore, this is accomplished without exposing any conductive portion of the straps and without the necessity of trimming the loose end of any strap.

Although the invention has been described with reference to specific embodiments, this description is not meant to be construed in a limiting sense. Various modifications of the disclosed embodiment, as well as alternative embodiments of the invention, will become apparent to persons skilled in the art upon reference to the description of the invention. It is therefore contemplated that the appended claims will cover such modifications that fall within the true scope of the invention.

I claim:

1. A device for electrically connecting an individual to a conductive grounding tether, comprising:
   a first strap having an electrically conductive portion for contacting a limb of the individual, said first strap having first and second ends, and an intermediate portion;
   a second strap which is elastic and electrically insulative, having first and second ends, said first end thereof being attached to said second end of said first strap;
   a connector case attached to said intermediate portion of said first strap, and having connector means for electrically connecting said conductive portion of said first strap to the tether;
   clasp means for adjusting the effective length of said second strap, said first end of said first strap being attached to said clasp means, and said second end of said second strap being attached to said clasp means; and
   first and second straps, connector case and clasp means defining a closed loop for encircling the limb of the individual.

2. The device of claim 1 wherein said first and second straps are integrally formed together, and both of said straps are elastic.

3. The device of claim 1 wherein said first strap has outer and inner surfaces, said outer surface thereof being electrically insulative and said inner surface thereof having an electrically conductive portion.

4. The device of claim 1 wherein said first strap is constructed from an elastic fabric having conductive yarns.

5. The device of claim 1 wherein said first strap is constructed from a chain of electrically conductive, expandable links.

6. The device of claim 1 wherein:
   said first strap is divided into first and second electrically isolated segments; and
   said connector means comprises first and second connectors, said first connector being in electrical contact with said first segment of said first strap, and said second connector being in electrical contact with said second segment of said first strap.

7. The device of claim 1 wherein:
   said second strap, connector case and clasp means define a closed loop which surrounds said first strap; and
   said first strap is flexible but inelastic.

8. A device for eliminating the buildup of an electrostatic charge on an individual, comprising:
   first strap means for contacting a limb of the individual, said first strap means having an electrically conductive portion, and first and second ends;
   a connector case attached to said conductive portion of said first strap means and having connector means for electrically connecting said conductive portion of said strap means to an electrically conductive tether;
   second strap means having first and second ends, said first end of said second strap means being attached to said second end of said first strap means, said second strap means being electrically insulative and elastic;
   clasp means for adjusting the effective length of said second strap means, said first end of said first strap means being attached to said clasp means, and said second end of said second strap means being attached to said clasp means, and said first and second strap means, connector case and clasp means defining a closed loop for encircling the limb of the individual.

9. The device of claim 8 wherein:
   said first and second strap means comprise a single integrally formed strap having first and second sections, said first section corresponding to said first strap means and said second section corresponding to said second strap means;
   said first strap section has outer and inner surfaces, said outer surface thereof being electrically insulative and said inner surface thereof containing said electrically conductive portion; and
   said strap is constructed from an elastic fabric having conductive yarns.

10. The device of claim 8 wherein said first strap means comprises a chain of electrically conductive, expandable links; and
    said second strap means comprises an electrically insulative, elastic fabric.

11. The device of claim 8 wherein:
    said first strap means comprises an inelastic but flexible fabric having electrically conductive yarns;
    said second strap means comprises an electrically insulative, elastic fabric; and
    said second strap means, connector case and clasp means define a closed loop which surrounds said first strap means, and further comprising guide means for aligning said second strap means with said first strap means.

12. The device of claim 8 wherein:
    said first strap means comprises a nonexpandable but flexible chain of conductive links;
    said second strap means comprises an electrically insulative, elastic fabric; and
    said second strap means, connector case and clasp means define a closed loop which surrounds said first strap means, and further comprising guide means for aligning said second strap means with said first strap means.

13. The device of claim 9 wherein:

said integrally formed strap is further divided into first and second electrically isolated segments, each having conductive portions; and said connector means comprises first and second connectors, said first connector being in electrical contact with said first segment of said strap, and said second connector being in electrical contact with said second segment of said strap.

14. The device of claim 10 wherein:

said chain of expandable links is further divided into first and second electrically isolated segments; and said connector means comprises first and second connectors, said first connector being in electrical contact with said first segment of said chain, and said second connector being in electrical contact with said second segment of said chain.

15. An adjustable wristband for dissipating excess electrostatic charge from an individual, comprising:

first, inelastic strap means for contacting a limb of the individual, said first strap means being electrically conductive at least along its inner surface, and constructed from an inelastic but flexible fabric having conductive yarns;

second, elastic strap means surrounding said first strap means, said second strap means being wider than said first strap means and being electrically insulative, and constructed from an elastic, electrically insulative fabric;

guide means for aligning said second strap means with said first strap means;

a connector case attached to said first and second strap means and having connector means for electrically connecting said first strap means to a grounding tether; and clasp means for adjusting the effective length of said second strap means, said first and second strap means, connector case and clasp means defining a closed loop for encircling the limb of the individual.

16. The device of claim 15 wherein:

said inelastic but flexible fabric is further divided into first and second electrically isolated segments; and said connector means comprises first and second connectors, said first connector being in electrical contact with said first segment of said inelastic but flexible fabric, and said second connector being in electrical contact with said second segment of said inelastic but flexible fabric.

17. An adjustable wristband for dissipating excess electrostatic charge from an individual, comprising:

first, inelastic strap means for contacting a limb of the individual, said first strap means being electrically conductive at least along its inner surface, and constructed from a nonexpandable but flexible chain of conductive links;

second, elastic strap means surrounding said first strap means, said second strap means being wider than said first strap means and being electrically insulative, and constructed from an elastic, electrically insulative fabric;

guide means for aligning said second strap means with said first strap means;

a connector case attached to said first and second strap means and having connector means for electrically connecting said first strap means to a grounding tether; and clasp means for adjusting the effective length of said second strap means, said first and second strap means, connector case and clasp means defining a closed loop for encircling the limb of the individual.

18. The device of claim 17 wherein:

said chain of conductive links is further divided into first and second electrically isolated segments; and said connector means comprises first and second connectors, said first connector being in electrical contact with said first segment of said chain, and said second connector being in electrical contact with said second segment of said chain.

* * * * *